United States Patent [19]
Eichhorn et al.

[11] Patent Number: 5,730,710
[45] Date of Patent: Mar. 24, 1998

[54] JOINT ORTHOSIS HAVING STIFFENABLE POCKET

[75] Inventors: Heinz-Jurgen Eichhorn; Michael Strobel, both of Mitterfels; Max Wensauer, Straubing; Gerard Sailler, Salching, all of Germany

[73] Assignee: Zimmermann Sanitats-und Miederhaus und Orthopädiebetrieb GmbH, Straubing, Germany

[21] Appl. No.: 774,316

[22] Filed: Dec. 24, 1996

Related U.S. Application Data

[63] Continuation of Ser. No. 657,528, Jun. 4, 1996, abandoned, which is a continuation of Ser. No. 270,777, Jul. 5, 1994, abandoned.

[30] Foreign Application Priority Data

Apr. 13, 1994 [DE] Germany .................. 44 12 765.0

[51] Int. Cl.$^6$ .................................................. A61F 5/00
[52] U.S. Cl. ...................... 602/26; 602/13; 602/16; 602/63
[58] Field of Search ................... 602/5, 13, 16, 602/23, 26, 61–63

[56] References Cited

U.S. PATENT DOCUMENTS

| | | | |
|---|---|---|---|
| 4,116,236 | 9/1978 | Albert | 602/26 |
| 4,219,892 | 9/1980 | Rigdon | 602/26 X |
| 4,287,885 | 9/1981 | Applegate | 602/26 |
| 4,366,813 | 1/1983 | Nelson | 602/26 |
| 4,378,009 | 3/1983 | Rowley et al. | 602/13 |
| 4,379,463 | 4/1983 | Meier et al. | 602/26 X |
| 4,872,448 | 10/1989 | Johnson, Jr. | 602/26 |
| 4,887,590 | 12/1989 | Logue et al. | 602/26 |
| 4,938,207 | 7/1990 | Vargo | 602/26 |
| 5,000,195 | 3/1991 | Neal . | |
| 5,154,690 | 10/1992 | Shiono | 602/26 X |
| 5,261,871 | 11/1993 | Greenfield | 602/26 |
| 5,263,926 | 11/1993 | Fujimoto | 602/62 |
| 5,316,547 | 5/1994 | Gildersleeve | 602/13 X |
| 5,334,135 | 8/1994 | Grim et al. | 602/62 X |
| 5,378,224 | 1/1995 | Billotti | 602/26 X |
| 5,385,538 | 1/1995 | Mann | 602/26 |

FOREIGN PATENT DOCUMENTS

| | | |
|---|---|---|
| 0 154 758 | 9/1985 | European Pat. Off. . |
| 3625952 | 2/1988 | Germany . |
| 36 37 879 | 5/1988 | Germany . |
| 1531268 | 12/1975 | United Kingdom . |
| WO 90/01307 | 2/1990 | WIPO . |

Primary Examiner—Linda C. Dvorak
Attorney, Agent, or Firm—Oblon, Spivak McClelland, Maier & Neustadt, P.C.

[57] ABSTRACT

A knee orthosis for conservative treatment of ligament injuries and post-operative support of the joint function, in particular for joint ligament-conserving damping of movement in the region of extreme flexion and/or extension positions. The joint orthosis has a bandage which is elastic at least region-by-region, envelops the joint, and rigidly encloses and thus fixes the movement apparatus in the region of the joint. The bandage exhibits in specific orthotic sections an integrated pocket or chamber system with which the joint orthosis can also be stabilized, optionally in interaction with pull or pressure stabilizer's of the bandage that are provided at suitable points, following attachment to the joint and following stiffening of the pockets, in such a manner that the joint can be moved beyond a specific angle of flexion and/or extension only if the joint orthosis absorbs the force.

21 Claims, 8 Drawing Sheets

JOINT ORTHOSIS HAVING STIFFENABLE POCKET

This application is a Continuation of application Ser. No. 08/657,528, filed on Jun. 4, 1996, now abandoned, which is a Continuation of application Ser. No. 08/270,777, filed on Jul. 5, 1994, now abandoned.

BACKGROUND OF THE INVENTION

1. Field of the Invention

The present invention relates to a joint orthosis, in particular knee orthosis.

2. Description of the Related Art

In the field of medicine and/or orthopedics, joints that have to be partially or totally immobilized can be immobilized with joint orthoses. In order to stabilize, for example, a knee joint following surgery of the cruciate ligament, one must take care that the extension of the knee joint is braked or damped in the last 10° of movement and/or the end stop is avoided, in order to avoid overstraining the operated on cruciate ligament. Especially when the cruciate ligament is ruptured, care must be taken that the so-called "drawer sign" is prevented. This "drawer sign" consists of the tibia being shifted forward relative to the femur when the stabilizing function of the cruciate ligaments is missing. In the case of a recently operated on cruciate ligament, the knee joint is allowed to perform only a damped extension, since especially in the final movement during leg extension the knee joint is held only by means of the ligaments arranged in the knee joint and laterally thereto.

Rigid and bulky frame or bar constructions that are difficult to build are usually used to immobilize the knee joint. With the aid of said rigid, bulky frame or bar constructions the knee joint's freedom of motion is restricted, said restriction being necessary for the convalescence process. Such frame constructions used as joint orthoses exhibit at least two orthotic sections, which are spaced for the purpose of attaching them to those regions of the patient's body that border the joint. These orthotic sections are connected together over orthotic regions that extend at least partially outside the center of the orthopedic device, thus achieving an immobilization of the joint or knee joint. On the other hand, the patient should be allowed to have a certain freedom of movement of the knee joint, in order to be able to maintain or train, for example, the musculature of the femur and tibia. In addition, if the knee joint has this freedom of movement, joint stiffness can be inhibited. For these reasons the conventional frame constructions are equipped with a flexing mechanism which rotates around a fixed point of rotation.

The drawback with these conventional frame constructions is that, when said knee joint is immobilized with a conventional frame construction, the knee joint can be bent only over a small range, since during flexing the point of rotation of the knee joint migrates due to the non-circular shape of the knee joint. Sometimes it can even happen that a point of rotation, which does not naturally exist in a knee joint to be treated, is forced on the knee joint by the pre-set flexing mechanism of the frame construction. Thus, the knee joint's ability to bend is restricted even more and/or causes the patient additional pain. This state occurs especially when, for example, the frame construction was not designed flexibly enough. Furthermore, the handling of the frame constructions is relatively complicated.

SUMMARY OF THE INVENTION

It is therefore an object of the present invention to provide a joint orthosis that is simple to manipulate and whose degree of moveability can be varied in a simple manner.

According to a feature of the invention, the joint orthosis exhibits at least one stiffenable pocket. With this functional feature the joint orthosis can be designed so as to be loose and flexible when being attached to that region of the patient's body that borders the joint. Thus, the joint orthosis can be adapted to the shape of the patient's body regions and can easily be stored and shipped in the non-stiffened state. Once the joint orthosis has been attached to the patient's region of the body the joint or knee joint can be stabilized or immobilized or specifically arrested by stiffening the pocket in the orthotic section. With this measure it is possible to control the immobilization or stabilization of the knee joint via the degree of stiffening, so that one can influence the immobilization necessary for the recovery of the joint to be treated. Thus, the orthosis according to the invention induces a stabilization of the joint without having to use complicated, bulky frame or bar constructions.

Furthermore, since the stiffened pocket exerts pressure on the musculature of the patient, the effect on the proprioreception of the musculature is positive and contributes in the post-operative phase to a decrease in swelling or to no swelling at all. In addition, the retroreceptors are affected, a state that causes the musculature to react faster.

According to the invention, the joint is stabilized in such a manner that the joint can be moved beyond specific angles of flexion and/or extension only if the joint orthosis absorbs the force.

The pocket can be stiffened in a simple manner, for example by inserting a filling medium or material. In particular, it is possible to stiffen the pocket with air, which can be introduced byway of a separately attachable pump or valve system. Furthermore, stiffening of the pocket can be accomplished with a fluid filling medium, which can be reversibly activated for stiffening chemically or electromagnetically.

If, for example, the maximum extension of the joint is to be limited by stiffening the pocket so that an extension of the joint is damped or more or less restricted, this function can be achieved by running the connection of the orthotic sections in the flexing region of the joint. With this design the orthotic sections are connected behind the joint's point of rotation so as to be preferably of high tensile strength. Thus, when the pocket is stiffened, the pull component of the pressure force on that region of the patient's body enveloped by the orthotic sections induces the joint to flex, said pull component being oriented in the connecting direction.

Since the joint orthosis of the invention does not exhibit a set or fixed point of rotation, one does not have to take into consideration a migrating point of rotation of the joint during flexion However, it is also possible to design the connection between the orthotic sections so as to be at least partially flexible so that the tensile force generated relative to the degree of flexion can be controlled via the degree of elasticity.

If the pocket is also arranged in the orthotic region opposite the region of flexion, then there is a high transfer of pressure, i.e. the tensile force component of the connection between the orthotic sections on the patient's region of the body is very high.

If there are at least two pockets which are inserted into the orthotic sections provided at those regions of the patient's body that border the joint, it is advantageous to design these pockets as a coupled system, so that the stiffening acts uniformly on both body regions. Only a single valve then has to be provided.

If the joint is bent while the pockets are stiffened, the result is a so-called shortening or compression effect, especially in the case of a knee joint, since the distance between two points, which are located on both sides of the joint and whose connecting line extends over the knee, grows during movement. To counteract the concomitant shortening or compression effect, it is advantageous to provide at least one stabilizer, which is arranged laterally to the plane of flexion in the joint orthosis. If the stabilizer is designed as a joint splint, which is also in the joint's region of flexion and has a flat spiral spring, then a migrating point of rotation of the joint can be accounted for in a simple manner.

To obtain optimal pressure transfer of the stiffened pockets to those regions of the patient's body that border the joint, the pocket is provided with a cover made of a nonelastic material, whereby the cover makes effective contact with the connection of the orthotic sections. Thus, it is guaranteed that the connection of the orthotic sections that induce the flexion of the joint simply puts volumetric expansion of the stiffened pocket at virtually the total disposal of the flexing action of the joint.

If the orthosis is formed as a bandage which is elastic region-by-region, the adaptation to the body regions of the patient can be accomplished in a very simple manner, whereby the design as a bandage also imparts a certain stability to the joint. For attachment, the orthosis can be provided with adjustable fasteners, so that those body regions of different patients that differ significantly in size can be taken into consideration, thus guaranteeing an exact attachment of the joint orthosis by means of adjustable fasteners.

If the fasteners are distributed at equal intervals over the joint orthosis, a uniform attachment and force distribution of the joint orthosis is enabled despite the different geometries and shapes of the body regions of the patient. If the fasteners are Velcro (i.e., hools and loop) fasteners, or roll fasteners, there is continuous adaptation to the shape of the regions of the patient's body.

In order to perform specific flexing actions of the joint, another pocket may be provided in the flexing region of the joint. When stiffened, this pocket produces another pressure point on the joint, which facilitates the flexing action according to a three point principle. However, it is just as possible to provide the orthosis with an opening in the flexing region of the joint if compression of the bandage material in the flexing region of the joint impedes recovery following a knee operation.

If the joint orthosis is formed by a neoprene bandage, the entire joint orthosis is flexible, whereby the neoprene bandage having a thickness of approximately 3 mm and lined with cotton on both sides is both compact and pleasant for the patient to wear. If the joint orthosis is slotted region-by-region in the flexing plane or the slot of the joint orthosis is lined region-by-region with an elastic material, the joint orthosis can be adapted to the geometry and shape of the regions of the patient's body.

If the joint orthosis is designed as an air chamber, the stiffening can be obtained in a simple manner, whereby deflation can readily be done. The air chambers can be incorporated into the orthotic sections, for example, as rubber bladders.

If the joint orthosis is provided with a ring, for example, with a patellar ring at a knee joint, which is mounted on the side of the joint orthosis facing the flexing region, the pressure can be taken off the knee cap, whereby a massaging effect of the ring on the musculature results in a decrease in swelling. An advantageous embodiment of the ring is a silicone ring.

BRIEF DESCRIPTION OF THE DRAWINGS

In the following, an embodiment of the invention will be explained in detail with reference to the schematic drawings in which.

DETAILED DESCRIPTION OF THE PREFERRED EMBODIMENTS

Figure 1:
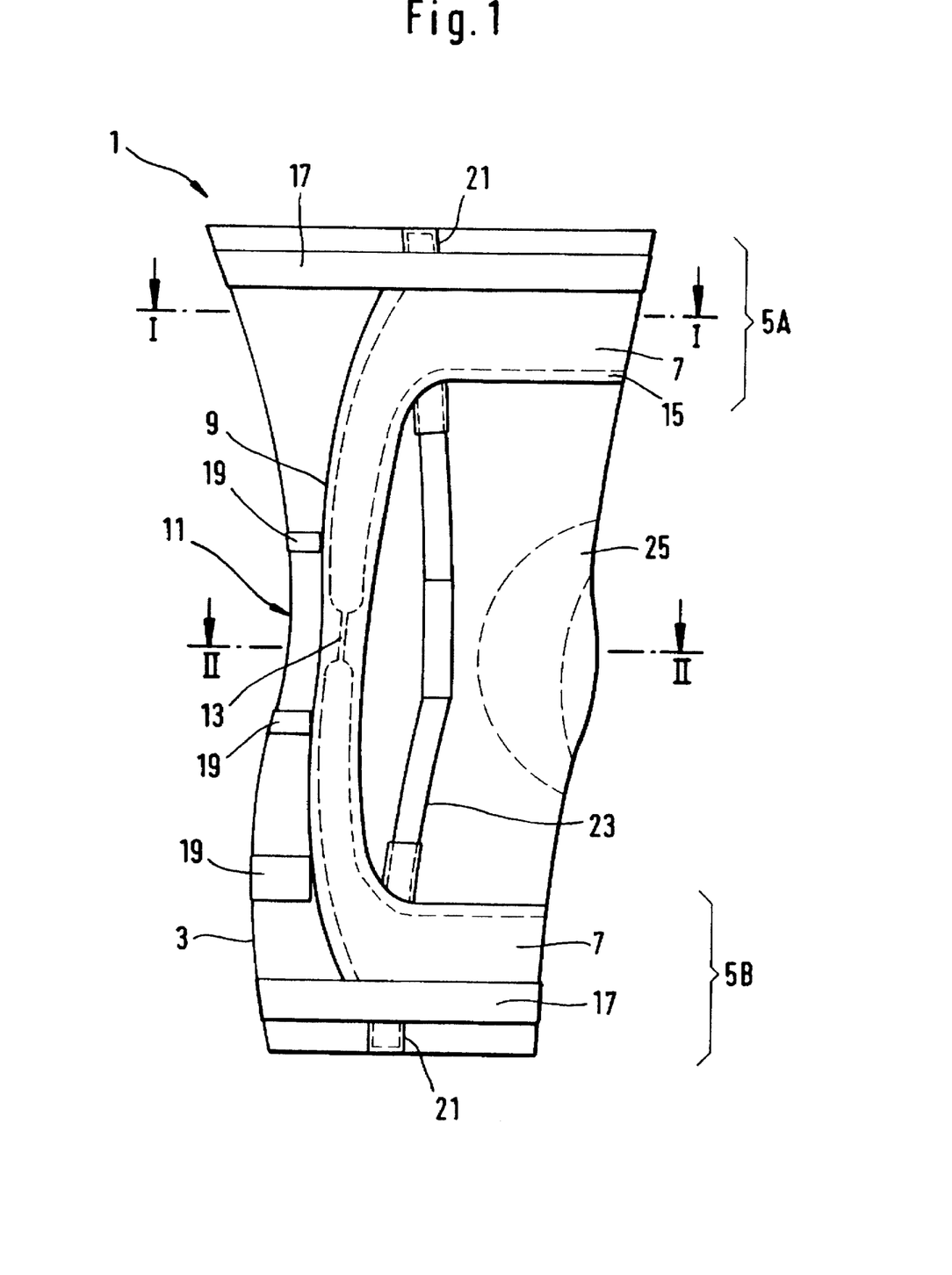
FIG. 1 is a side view of a joint orthosis according to the invention.

FIG. 1 depicts an embodiment in the form of a knee orthosis 1, which is designed as a bandage 3, which is intended preferably for flexion and exhibits two orthotic sections 5A, 5B. Into each orthotic section 5A, 5B is integrated ventrally a pocket 7 in the form of an air chamber, both sections being connected together via a connection 9 which extends in the bending region or flexing region 11 of the knee joint.

As shown in FIG. 1, the pockets 7 in the bending region 11 of the joint orthosis 1 are connected preferably via a thin channel 13 which is large enough to allow pressure equalization between the air chambers and is small enough not to excessively inhibit excessive flexing. Should the stiffening of the pockets 7 reach such a degree that the connecting channel 13 has a deleterious effect on the flexing action of the knee joint, it is advisable to design the pockets 7 separately from each other and to adapt correspondingly the extension of the pockets 7 in the connecting section 9a.

As also shown in FIG. 1, the air chambers extend ventrally, distally, and also proximally at right angles and dorsally at an oblique angle behind the anatomical point of rotation of the knee joint relative to the hollow of the knee, i.e., in the direction of the bending region 11. The distal and proximal pockets 7 are provided with a cover 15 in such a manner that especially those regions of the pockets that run at right angles to the longitudinal axis of the leg are provided with non-elastic material, so that the volumetric expansion of the air chambers is oriented in the direction of the body regions of the patient.

To reinforce this targeted volumetric expansion as the pockets 7 are stiffened, the cover is preferably designed as a rigid cover enclosing the pockets 7, and/or a strip 17 is attached to the cover 15. Said strip wraps circularly around the body regions of the patient and is designed as a fastener, preferably a Velcro fastener, which can be closed preferably in the dorsal region. In addition, there are other fasteners 19 which are attached preferably only in the bending region 11. The number of Velcro fasteners can be coordinated with the length of the joint orthosis in order to enable an optimal adaptation to the body regions of the patient.

Moreover, the joint orthosis 1 according to the invention has holding mechanisms 21 into which at least one stabilizer 23 can be inserted, on each side of the joint orthosis 1. The stabilizer 23 is designed as a joint splint which serves to prevent the shortening or compression effect of the joint orthosis during the flexing operation action, which might otherwise be induced by the stiffening of the pockets. The shortening or compression effect of the joint orthosis is induced by pull loading on the covers 15, in the dorsal region or in the bending region 11, during extension. The consequence is that the elastic orthosis is pulled together and no extended leg position is reached. The stabilizers 23 are braced preferably at the proximal or distal outer region of the knee orthosis.

The side of the joint orthosis opposite the flexing region 11 has a ring 25, which in the case of a knee orthosis causes pressure relief at the knee cap and promotes a decrease in swelling owing to its massaging effect. The ring can be incorporated into the joint orthosis and also mounted preferably on the inner surface of the joint orthosis 1. If the holding mechanisms 21 extend from the outer region of the joint orthosis 1 as far as up to the bending region 11 of the joint orthosis 1, the result is an advantageous guide of the stabilizers 23.

Figure 2:
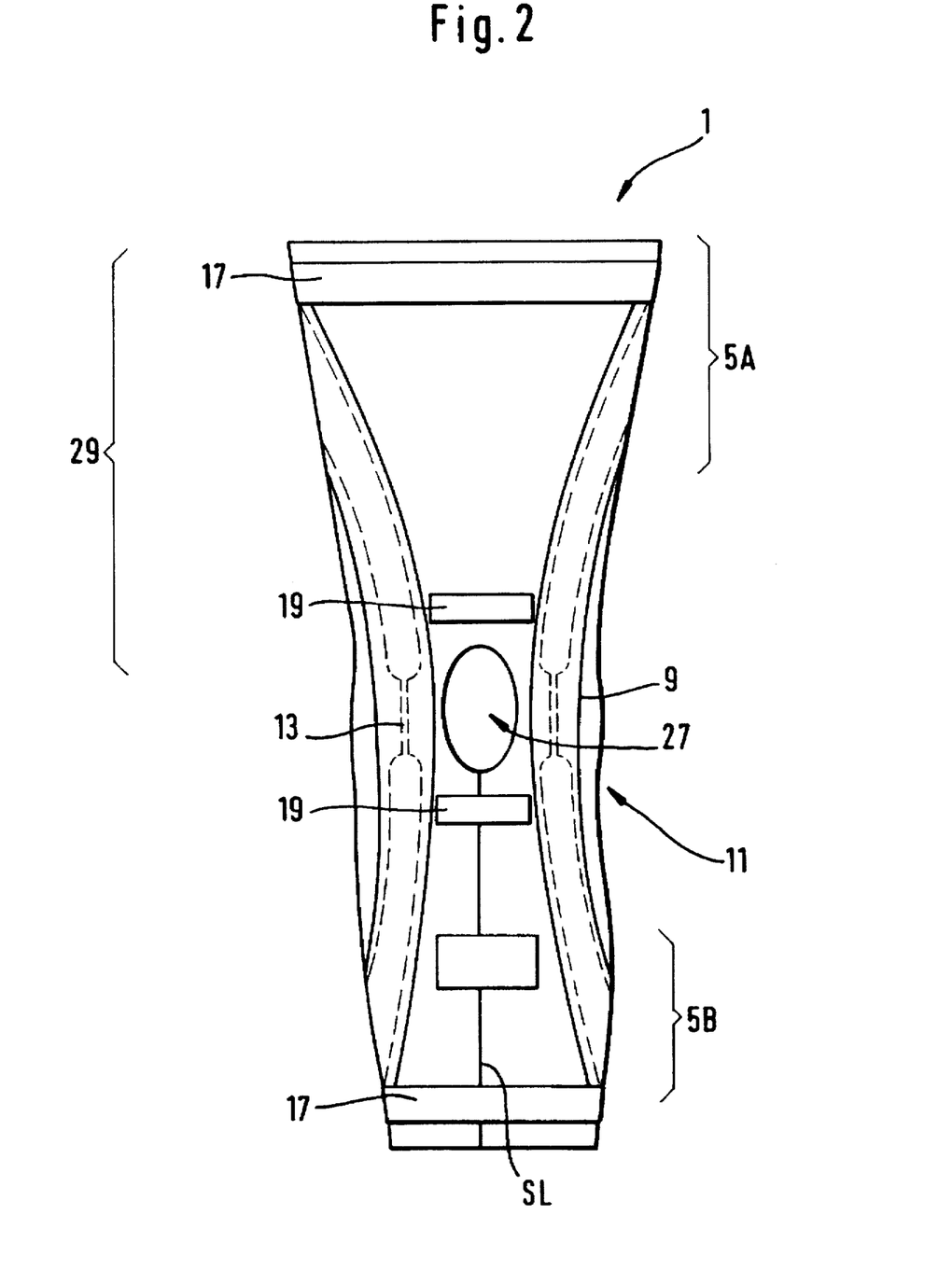
FIG. 2 is a rear view of the joint orthosis according to FIG. 1.

FIG. 2 is a rear view of the joint orthosis 1 according to FIG. 1. It may clearly be seen from this drawing how the preferably pull-proof and non-extensible connection 9 between the orthotic sections 5A, 5B runs in the flexing region 11. By means of this arrangement of the connections 9, a kind of cross connection in the flexing region 11 is simulated that prevents or limits the full extension of the joint. As shown in FIG. 2, the connections 9 of the orthotic sections 5A, 5A are positioned laterally relative to the longitudinal center axis of the joint orthosis 1.

However, it is also possible to cross the connection between the orthotic sections 5A, 5B in such a manner, that there is, in fact, a cross connection, comparable to "hyperextension belts". Care must then be taken that the diameter of the channel 13 is tuned in such a manner that the flexion or bending is not restricted any more than with the commercially available knee bandage. If the connections cross, it is advantageous to form both pockets separately from each other and to equip the air chambers with a separate pump and valve system, so that there is no additional constriction in the bending region 11.

To counteract a material compression of the joint orthosis 1, an opening 27 can be provided especially in the flexing region.

Figure 4:
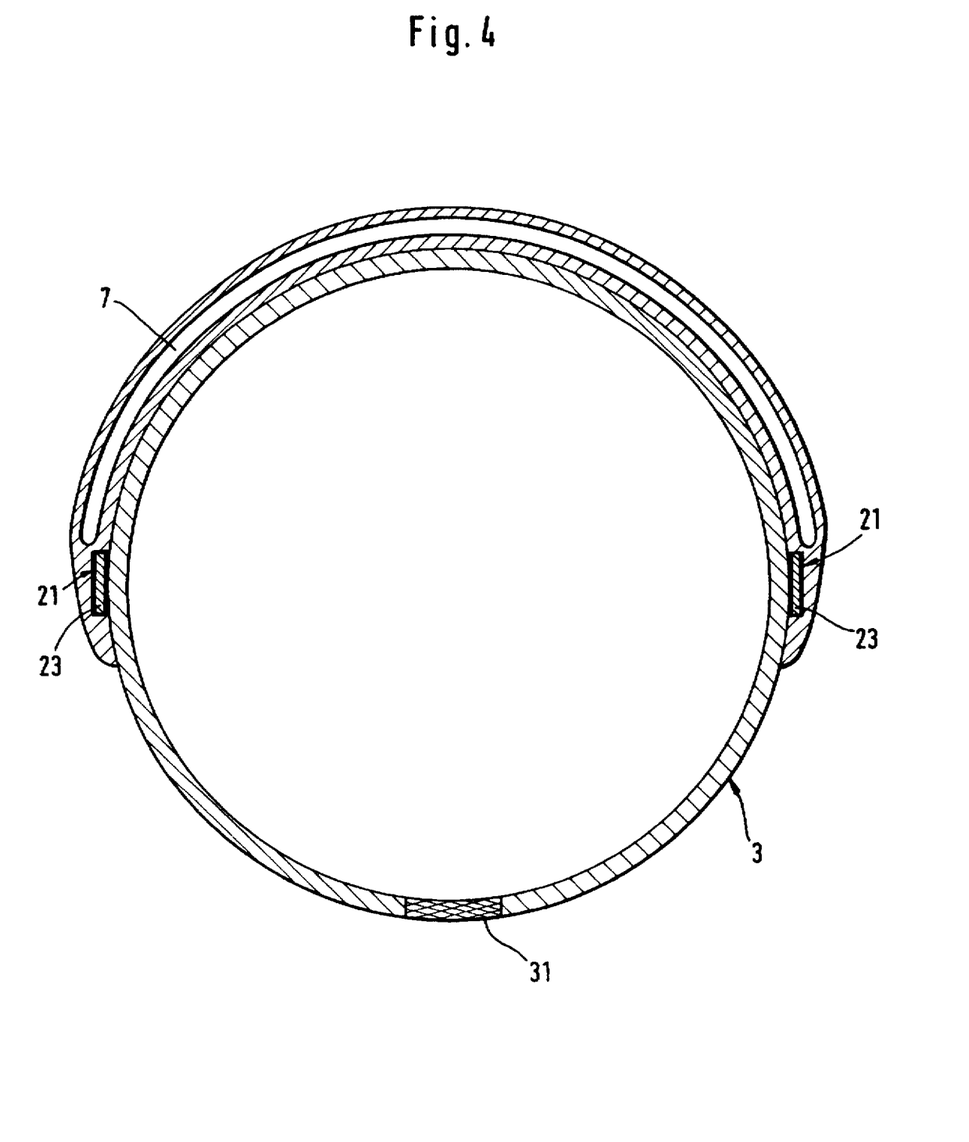
FIG. 4 is a sectional view along the line I—I in FIG. 1.

As evident from FIG. 2, the strips 17, which extend circularly, and the Velcro fasteners 19, can be clearly recognized. The joint orthosis i is slotted along the cut line SL. In the proximal region 29 of the joint orthosis 1, the slot SL is lined with an elastic material 31. However, this lining can be provided, for example, only region-by-region. The elastic material 31 (FIG. 4) is attached to the slot edges of the joint orthosis 1.

Figure 3:
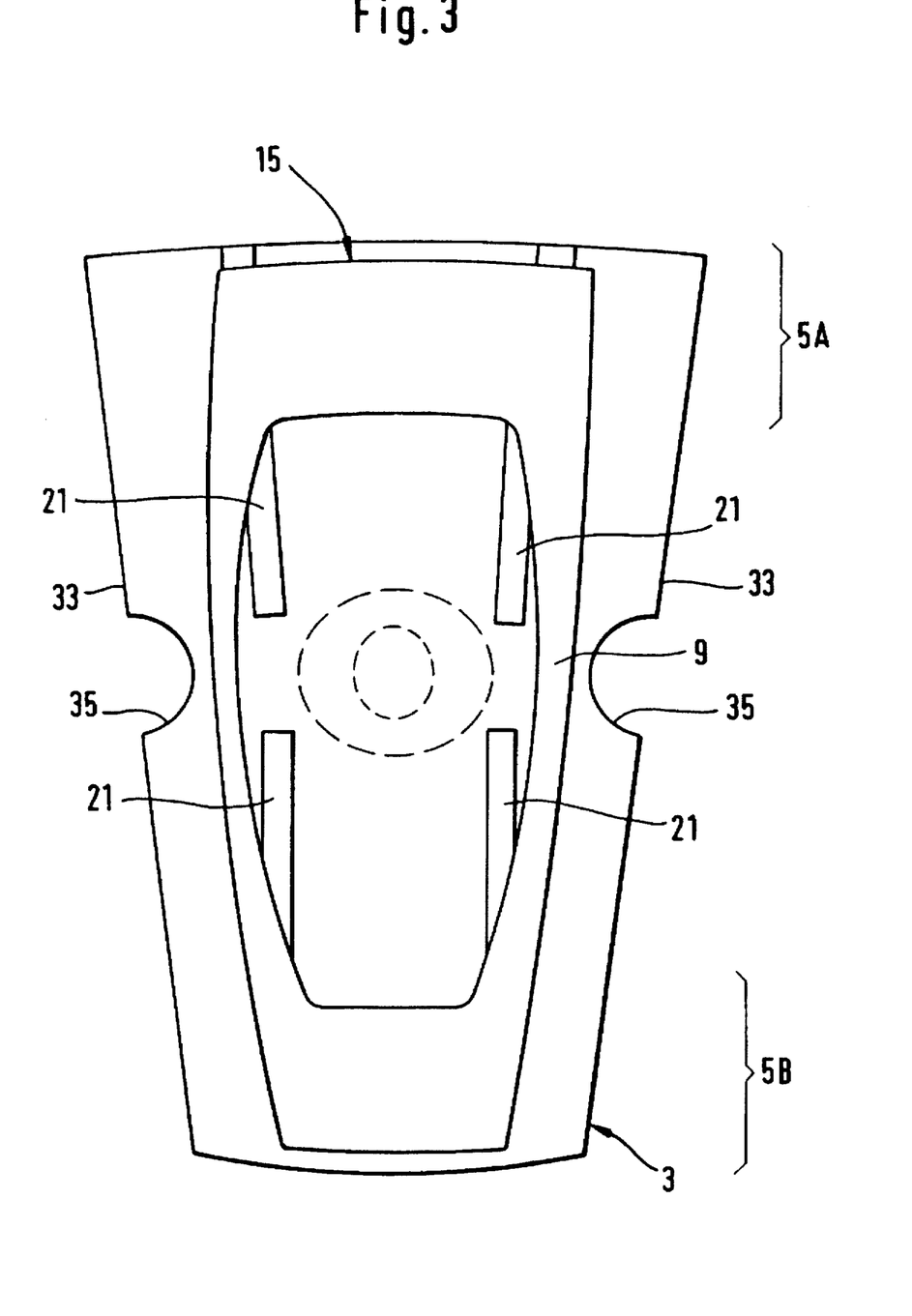
FIG. 3 is a front view of the joint orthosis according to FIG. 1 in the spread-out state.

FIG. 3 depicts the joint orthosis I in the spread-out state without stabilizers for vertical stiffening and without Velcro fasteners. This drawing shows the entire cover 15 and the connection 9 between the orthotic sections 5A, 5B. In the case of a knee orthosis, a conically tapering leg is taken into account by making the proximal terminal edge larger than the distal terminal edge of the joint orthosis 1. The consequence is that the joint orthosis is trapezoidal, as shown in FIG. 3.

The side edges 33 of the joint orthosis 1 have semicircular recesses 35, which yield the opening 27 when the joint orthosis is in the attached state. The joint orthosis 1 is not limited to the circular recesses. However, care should be taken that the recesses are designed in such a manner that the material is prevented from compressing during the flexing action of the joint orthosis.

Laterally with respect to the center of the orthosis there are holding mechanisms 21, which are mounted preferably directly on the bandage 3 and are covered by the cover or the underlying pockets 7. This advantageous embodiment of the joint orthosis is clearly highlighted in FIG. 4, which reproduces a cut along the cutline I—I of FIG. 1. In the bandage 3, enveloping the body region of the patient, the elastic material 31 inserted into the slot can be recognized, as can the nonelastic cover with the accommodated pockets 7 and the holding mechanisms 21 for insertion of the stabilizers 23 which envelops the bulk of the bandage 3.

Figure 5:
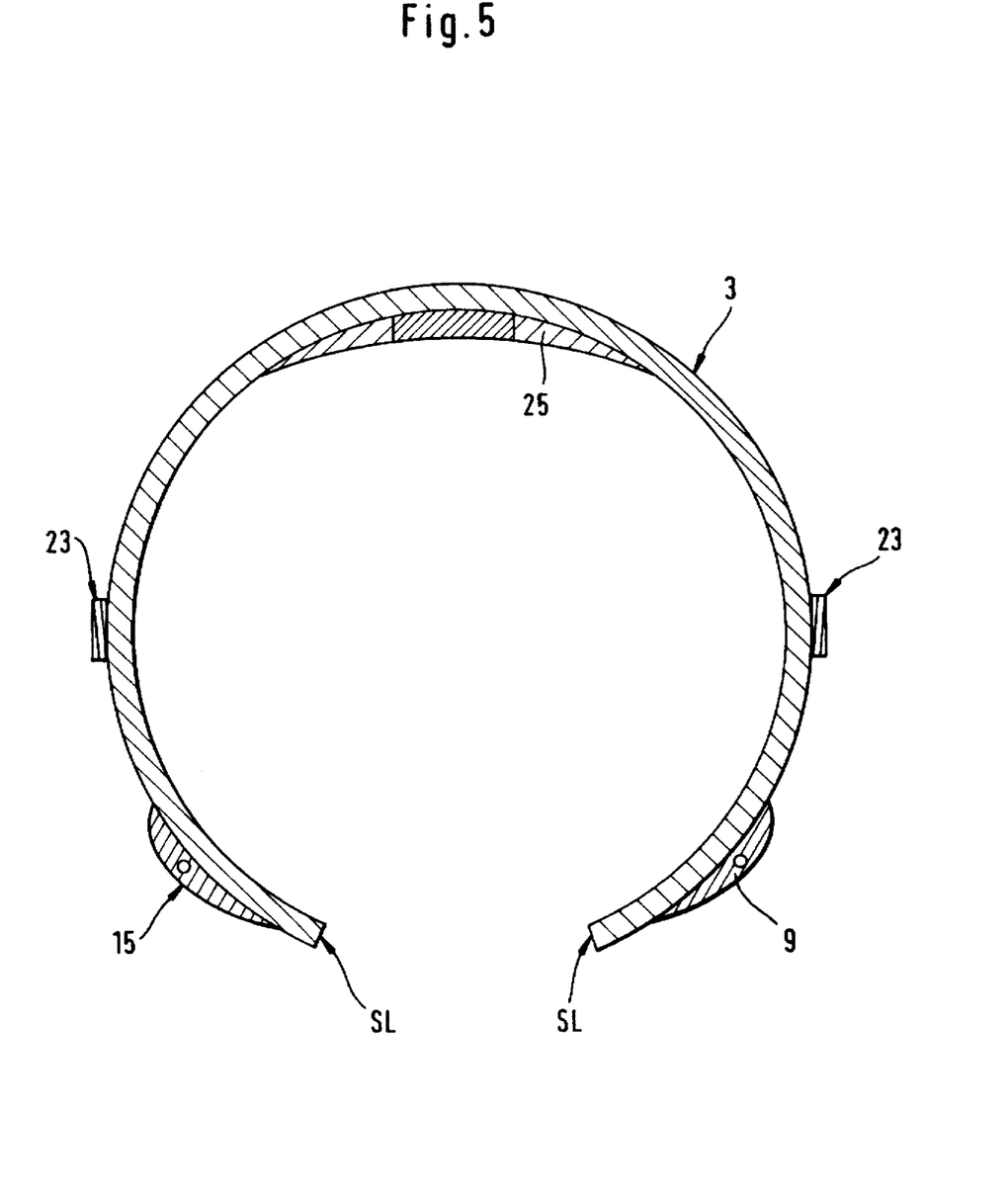
FIG. 5 is a sectional view along the line II—II of FIG. 1.

FIG. 5 is a sectional view along the cutline II—II of FIG. 1 in the flexing region 11. It may be seen that the connection 9 between the pockets 7 in the orthotic sections 5A, 5B, and the connection of the cover 15 in the flexing region 11, extend close to the cut edge of the cut line SL in order to enhance the cross connection between the orthotic sections 5A, 5B in the dorsal region.

The neoprene bandage 3, which wraps itself almost completely around the leg, exhibits laterally with respect to the center of the orthosis the stabilizers 23 for vertical stiffening and on the side opposite the flexing region 11, a ring 25 made, for example, of silicone, which is attached preferably to the inside of the joint orthosis, i.e., the bandage 3.

Figure 6:
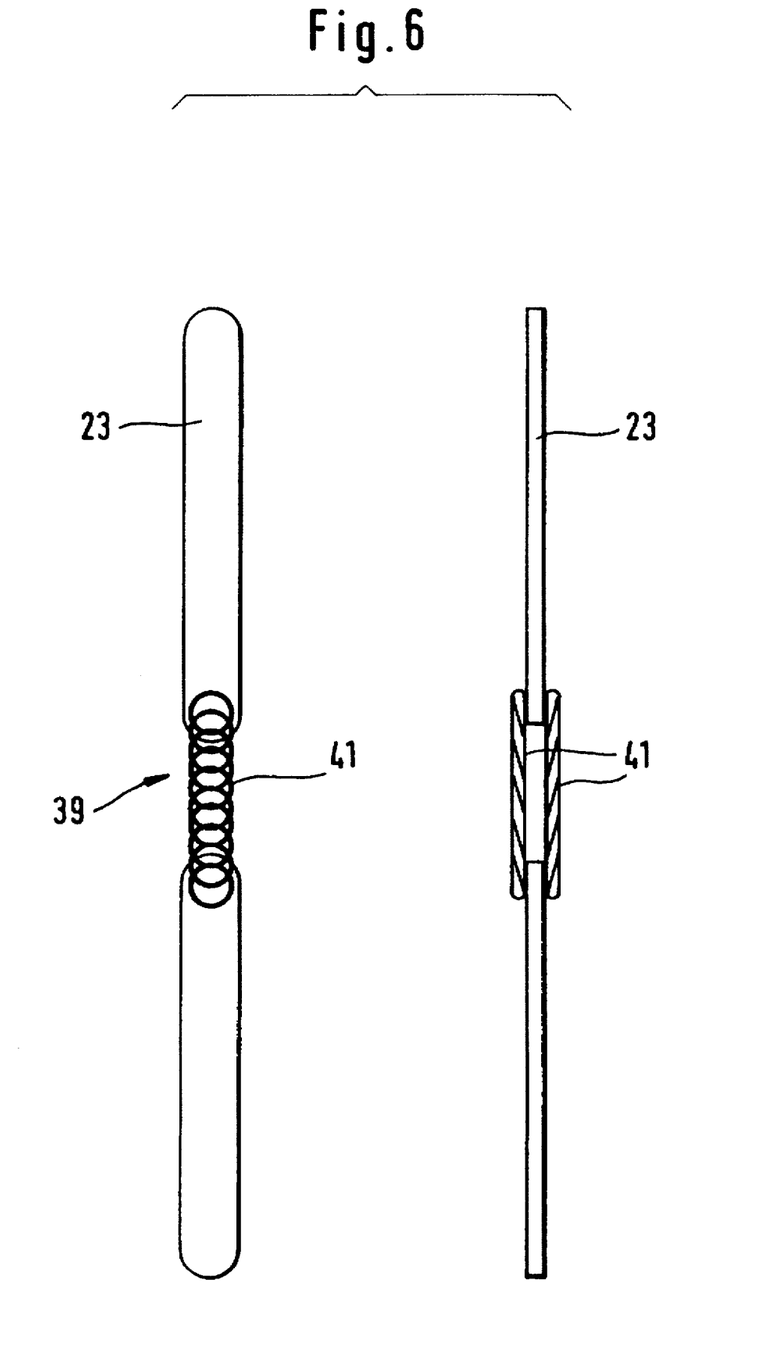
FIG. 6 is a front and side view of lateral stabilizers of a joint orthosis according to the invention.

FIG. 6 is a side and rear view, for examples of one type of stabilizer 23. This stabilizer designed as a joint splint exhibits two steel strips, for example 15×1.5 mm, which are connected together via flexible or elastic elements 39. The flexible or elastic elements 39 are made preferably of flat springs 41 whose length is tuned to the existence of a migrated point of rotation of the joint in such a manner that the flexing action of the joint orthosis 1 is not prevented. Furthermore, by using joint splints having different spring constants, one can affect both the patient to be treated and the recovery process of the joint.

The embodiment described above is designed in such a manner that, when the joint orthosis is in the attached state, fixed via the Velcro fasteners to the leg, the air chambers extend in such a manner that, in addition to the stiffening function, they counteract a certain resistance, starting from a certain angle of flexion in the extension process, via the air chambers, which air chambers have routinely less elasticity than the bandage.

Figure 7:
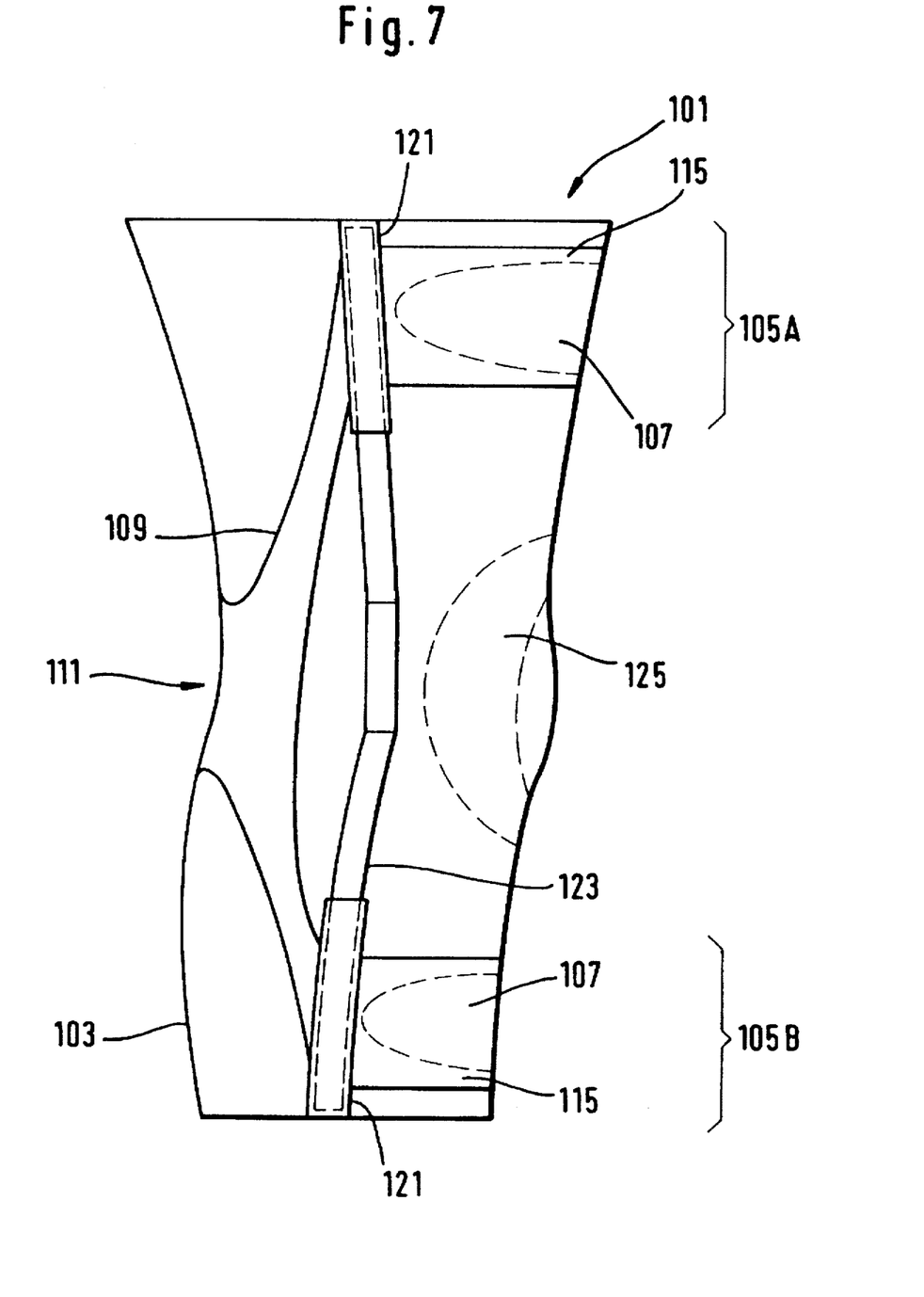
FIGS. 7 and 8 are comparable views to FIGS. 1 and 2 of another embodiment of the knee orthosis.
Figure 8:
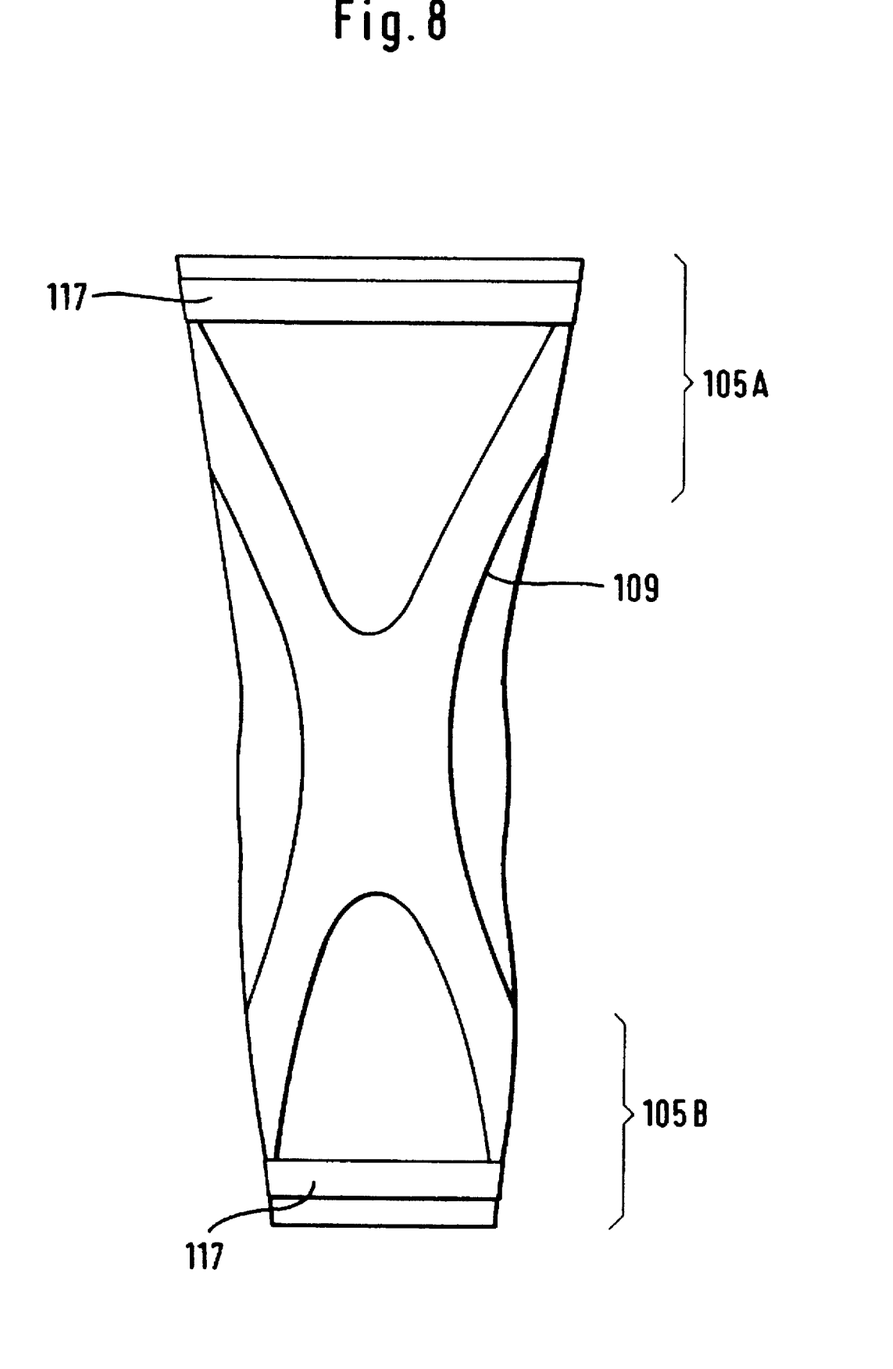

In the embodiment according to FIG. 7, in which those components that are comparable to components of the embodiment described first are marked with identical reference numerals, but increased by "100", there is in the flexing region of the knee orthosis an essentially X-shaped sew-on 109, which connects together so as to be pill-proof the orthotic sections 105A, 105B. In this case the air-pockets 107 can be designed with less volume, as evident from the side view according to FIG. 8.

At this point it shall be noted that one can also dispense with the stabilizers, if the joint orthosis is fastened in such a manner that no compression or shortening effect of the joint orthosis can occur when the pocket is stiffened.

Thus, the present invention provides a joint orthosis, in particular a knee orthosis, for conservative treatment of ligament injuries and post-operative support of the joint function, in particular for joint ligament-conserving damping of movement in the region of extreme flexion and/or extension positions. The joint orthosis has a bandage which is at least partially elastic, envelops the joint, and rigidly encloses and thus fixes the movement of the apparatus in the region of the joint. The bandage exhibits in specific orthotic sections an integrated pocket or chamber system with which the joint orthosis can also be stabilized, optionally in interaction with pull or pressure stabilizers of the bandage that are provided at suitable points, following attachment to the joint and following stiffening of the pockets, in such a manner that the joint can be moved beyond a specific angle of flexion and/or extension only if the joint orthosis absorbs the force.

Obviously, numerous modifications and variations of the present invention are possible in light of the above teachings. It is therefore to be understood that within the scope of the appended claims, the invention may be practiced otherwise than as specifically described herein.

What is claimed:

1. A knee joint orthosis comprising:

at least two orthotic sections respectively fastenable to parts of the patient's body that border a joint;

a connection connecting together said orthotic sections over orthotic regions of the joint that extend at least partially outside a center of the orthosis;

at least one inflatable stiffenable pocket formed in at least one of the orthotic sections and being coupled to at least a portion of said connection positioned at a flexing region substantially behind an anatomical point of rotation of the joint when the joint is at an extreme extension position; and means for securing said orthotic sections to said parts of the patient's body that border a joint, wherein said connection connects together said orthotic sections such that said connection is positioned at the flexing region substantially behind an anatomical point of rotation of the joint when the joint is at an extreme extension position and the orthosis is fastened to the patient's body by said orthotic sections, whereby movement of the joint to an extreme extension position is damped.

2. Joint orthosis as claimed in claim 1, wherein said at least the one pocket is stiffened with a filling medium.

3. Joint orthosis as claimed in claim 1 wherein the connection connects the orthosis sections in a flexing region of the joint when the orthosis is fastened around the joint.

4. Joint orthosis as claimed in claim 2 wherein said filling medium is air, wherein at least one of said stiffenable pockets is formed in each of said orthotic sections, and wherein said stiffenable pockets in said orthotic sections are coupled together so that the air can communicate between the two.

5. Joint orthosis as claimed in claim 1 including at least one stabilizer arranged laterally to the plane of flexion of the joint when the orthosis is fastened around the joint.

6. Joint orthosis as claimed in claim 5 wherein said at least one stabilizer comprises a joint splint.

7. Joint orthosis as claimed in claim 6 wherein the joint splint has a flat spiral spring in the joint's region of flexion when the orthosis is fastened around the joint.

8. Joint orthosis as claimed in claim 1 wherein said at least one pocket is covered with a cover made of a nonelastic material.

9. Joint orthosis as claimed in claim 1 wherein said orthosis comprises a bandage which is at least partially elastic, and wherein said at least one stiffenable pocket is secured to said bandage.

10. Joint orthosis as claimed in claim 9 wherein said securing means includes adjustable fasteners mounted to said bandage.

11. Joint orthosis as claimed in claim 10 wherein the fasteners are distributed at equal intervals on the bandage.

12. Joint orthosis as claimed in claim 10 wherein the fasteners are one of hoop and loop fasteners and roll fasteners.

13. Joint orthosis as claimed in claim 9 including at least one of said stiffenable pockets in said bandage.

14. Joint orthosis as claimed in claim 9 including an opening within the flexing region of said bandage.

15. Joint orthosis as claimed in claim 9 wherein the bandage is formed as a neoprene bandage.

16. Joint orthosis as claimed in claim 9 wherein said bandage has a slot in the region of flexion when the orthosis is fastened around the joint.

17. Joint orthosis as claimed in claim 16 wherein the slot is a region of lines partially filled with an elastic material which can be connected to edges of the slot.

18. Joint orthosis as claimed in claim 1 wherein said at least one pocket comprises an air chamber.

19. Joint orthosis as claimed in claim 18 including a valve attachable to the air chamber.

20. Joint orthosis as claimed in claim 9 including a patellar ring in said bandage.

21. Joint orthosis as claimed in claim 20 wherein the patellar ring is made of silicone.

* * * * *